(12) United States Patent
Musahl et al.

(10) Patent No.: US 9,949,684 B2
(45) Date of Patent: Apr. 24, 2018

(54) QUANTIFIED INJURY DIAGNOSTICS

(71) Applicant: UNIVERSITY OF PITTSBURGH—OF THE COMMONWEALTH SYSTEM OF HIGHER EDUCATION, Pittsburgh, PA (US)

(72) Inventors: Volker Musahl, Pittsburgh, PA (US); Yuichi Hoshino, Kobe (JP); Paulo Henrique Mendes De Araujo, Brasilia (BR); Mattias Ahlden, Gothenburg (SE); James Irrgang, Murrysville, PA (US); Freddie H. Fu, Pittsburgh, PA (US); Richard E. Debski, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 326 days.

(21) Appl. No.: 14/362,015

(22) PCT Filed: Dec. 5, 2012

(86) PCT No.: PCT/US2012/067968
§ 371 (c)(1),
(2) Date: May 30, 2014

(87) PCT Pub. No.: WO2013/086009
PCT Pub. Date: Jun. 13, 2013

(65) Prior Publication Data
US 2014/0316242 A1    Oct. 23, 2014

Related U.S. Application Data

(60) Provisional application No. 61/566,761, filed on Dec. 5, 2011.

(51) Int. Cl.
*A61B 5/00* (2006.01)
*A61B 5/11* (2006.01)

(52) U.S. Cl.
CPC .......... *A61B 5/4528* (2013.01); *A61B 5/1127* (2013.01); *A61B 5/1128* (2013.01);
(Continued)

(58) Field of Classification Search
None
See application file for complete search history.

(56) References Cited

U.S. PATENT DOCUMENTS 4,631,676 A    12/1986 Pugh
2006/0241405 A1    10/2006 Leitner et al.
(Continued)

OTHER PUBLICATIONS

The International Search Report and the Written Opinion of the International Searching Authority, PCT/US2012/067968, dated Apr. 1, 2013, 10 pages.

*Primary Examiner* — Tse Chen
*Assistant Examiner* — Jason Ip
(74) *Attorney, Agent, or Firm* — Eckert Seamans Cherin & Mellott, LLC; Philip E. Levy

(57) ABSTRACT

A new and/or novel image analysis technique for quantitative assessment of motion-based testing for injury in a patient using universally available and affordable devices and techniques is provided and disclosed. A video of a test being performed can be processed to track the motion of markers and/or bodily landmarks in two or more dimensions to quantitatively describe motion, thereby removing the subjective aspects typically associated with motion-based testing. In an example, the pivot shift test is a commonly used test for evaluating rotational instability of the anterior cruciate ligament (ACL)-deficient knee. The pivot shift test's subjective grading scale can be quantified and refined using image analysis techniques.

20 Claims, 11 Drawing Sheets

(52) U.S. Cl.
CPC .......... *A61B 5/4533* (2013.01); *A61B 5/4585* (2013.01); *A61B 5/0022* (2013.01)

(56) References Cited

U.S. PATENT DOCUMENTS

| | | | |
|---|---|---|---|
| 2007/0016109 A1* | 1/2007 | Orito | A61B 5/1114 |
| | | | 600/595 |
| 2008/0183108 A1 | 7/2008 | Huber et al. | |
| 2008/0194997 A1* | 8/2008 | Zhang | A61B 5/1071 |
| | | | 600/595 |
| 2009/0135185 A1* | 5/2009 | Demizu | G06T 19/00 |
| | | | 345/427 |
| 2010/0234770 A1* | 9/2010 | Colombet | A61B 5/064 |
| | | | 600/595 |
| 2011/0116688 A1* | 5/2011 | Li | G01N 33/0098 |
| | | | 382/110 |

* cited by examiner

QUANTIFIED INJURY DIAGNOSTICS

CROSS-REFERENCE TO RELATED APPLICATIONS

This application is related to U.S. Provisional Patent application Ser. No. 61/566,761 entitled "IMAGE ANALYSIS METHOD TO QUANTIFY THE LATERAL PIVOT SHIFT TEST" and filed Dec. 5, 2011 and claims the benefit thereof. The entirety of the above-noted application is incorporated by reference herein.

TECHNICAL FIELD

The subject innovation relates to the field of medical treatment and, more specifically, pertains to methods and systems for providing repeatable, objective analysis of rotational instability in joints and other conditions.

BACKGROUND

The human body can engage in a vast range of motions. Such motion is constrained according to a variety of tissue types. For example, ligaments are fibrous tissues that can connect bone and can limit the direction and distance of motion in various dimensions that bones can move with respect to one another.

In a specific example, the anterior cruciate ligament (hereinafter, "ACL") is one of the four major ligaments of the human knee. The ACL originates from deep within the notch of the distal femur. Its proximal fibers fan out along the medial wall of the lateral femoral condyle. The ACL has two bundles: the anteromedial and the posterolateral. Each bundle is named in accordance with where the bundles insert into the tibial plateau.

The ACL attaches in front of the intercondyloid eminence of the tibia, being blended with the anterior horn of the medial meniscus. These attachments allow it to resist anterior translation and medial rotation of the tibia, in relation to the femur.

Various ligaments and other bodily tissues (e.g., the ACL) can be injured in such a way that motions involving such tissues become abnormal. Continuing discussion with respect to the ACL, damage to this ligament is a very common injury, especially in the context of sporting events and other physically rigorous activity. Most often, the ACL is sprained or torn due to rapid, unintentional lateral rotational movements caused by impacts from external forces or falling unexpectedly. Less serious sprains can frequently be addressed by way of physical therapy and muscle strengthening exercises. Tears, on the other hand, almost always require arthroscopic surgery to address.

The health of ligaments and other tissues can be assessed (e.g., to determine injury, to assess recovery after treatment) at least in part by determining the presence or absence of rotational instability and/or abnormal motion. For example, injury to the ACL can be diagnosed by evaluating ligamentous laxity in the knee. The lateral pivot shift test is widely used to evaluate rotational instability after ACL injury and treatment. Traditionally, the result of this test is subjectively determined by the examiner and therefore highly variable. There is presently no widely attainable quantitative evaluation system which can be used in clinical practice despite extensive research efforts to measure rotational instability in the knee or other joints in the human body.

One cause for the lack of an earlier objective evaluation system for rotational instability is the complexity of both normal and abnormal movements. For example, the lateral pivot shift test performed on the ACL evaluates the pivot shift movement. The pivot shift is a six degree-of-freedom movement, including tibial internal-external (i-e) rotation, varus-valgus (v-v) rotation, and anterior-posterior (a-p) translation. Subjective assessment can be used to assign a grade denoting the results of the lateral pivot shift test. Grade I can indicate relatively mild injury that demonstrates abnormal movement when the tibia is held in maximal medial rotation. Grade III (or higher, in some variants) indicates a relatively severe injury that manifests as significant, sudden abnormal movement when the tibia is held in neutral or moderate lateral rotation. Various techniques can attempt to detect abnormal motion by employing invasive navigation systems employing pins fixed into bone to demonstrate correlation between a-p translation of the lateral compartment and the results of the clinical pivot shift test grade.

Most reported devices used in experimental trials of measurements for determining rotational instability (e.g., pivot shift measurement), such as navigation systems and/or electromagnetic sensors and accelerometers, are not universally available. Further, even where available, such devices are costly and require specialized support to practice. Further, although various kinematic assessments have been conventionally used for qualitative evaluation of the pivot shift test, there is no clinically available quantification technique for assessing rotational or other instability. Thus, there is a need in the art for systems and methods to visually quantify such diagnostic values (e.g., quantification of a lateral pivot shift test).

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

In various aspects, the innovation can include a system comprising at least a capture component, a still analysis component, and a condition assessment component. The capture component can record video or a series of images that can be analyzed to measure the movement of various aspects within the image. The condition assessment component can determine a medical condition based at least in part on motion quantified by the still analysis component. In an example, abnormal motion can be identified based on associated quantities established through analysis of a recording, thereby eliminating the subjectivity that frequently accompanies such examination.

In embodiments, markers can be used to denote the points for which motion is measured. For example, stickers or various other applied markings can be put on bodily landmarks (e.g., bony protrusions) to facilitate their tracking in a non-invasive manner. A marker identification component can be used to emphasize and track these markers automatically throughout analysis.

Additional aspects can include various image processing and optimization components used to improve the quality of captured images or analyses related thereto. Various converters can be used to facilitate interoperability between devices and software involved in recording and analysis of testing, and presentation of results.

A scaling component can be included in one or more system embodiments that facilitate scaling of the image or depicted aspects to absolute or relative units. In some embodiments, scaling can be automatic based on a provided value (e.g., the size and shape of a marker).

In further aspects of the innovation, embodiments of can include performing a motion-based test related to two or more identifiable points, recording performance of the motion-based test in a plurality of frames, and measuring a plurality of movements of the two or more identifiable points between consecutive frames among the plurality of frames. In this way, abnormal motion in a patient's joint can be detected. Other aspects such as marking the identifiable points can also be included.

Motion can be measured according to or applied to various coordinate systems. In this way, tables and graphs of motion can be presented based on a coordinate location of one or more points on the coordinate system.

Still further, the motion-based test can be performed a number of times, ensuring successful capture of an iteration suitable for capture, and also allowing multiple analyses to be run to determine maximums, minimums, averages, and so forth.

Still further, an accelerometer (e.g., hardware, software, combination thereof, included in a dedicated device or as a sub-aspect thereof) can be used to assist the tracking of abnormal joint motion. Aspects can include the use of an accelerometer in, for example, a smart phone or other mobile device.

Other aspects will be apparent to those skilled in the art based on the disclosures herein.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
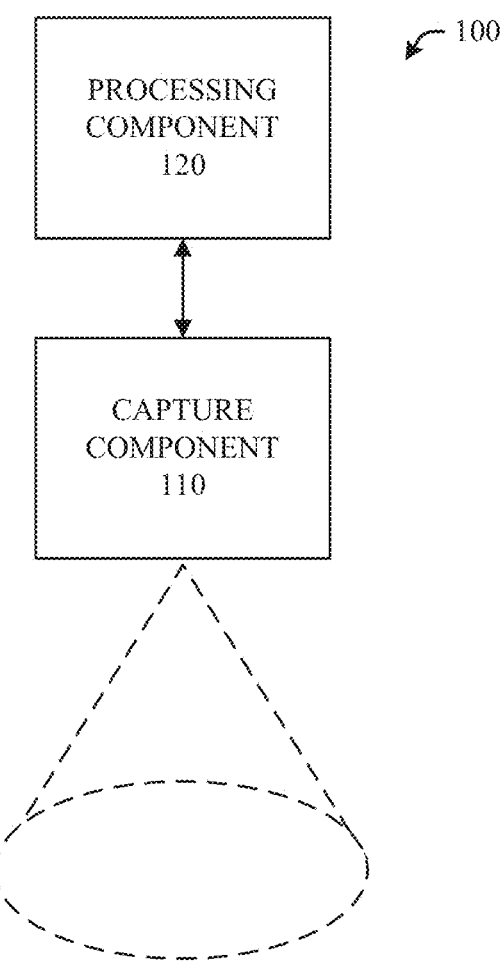
FIG. 1 illustrates a system that processes images to render medical information.

The innovation includes a novel image analysis technique for quantitative assessment of motion-based diagnostic tests (e.g., pivot shift test) using widely available and affordable devices and/or software. The disclosures herein satisfy the need for affordable, non-proprietary techniques that utilize kinematic measurements to determine injury (e.g., to the ACL). Systems and methods can be employed to facilitate, record and analyze motion-based testing in the human body. Analysis performed can provide a diagnosis, including grading or quantitative valuation of, injury to a tested body part. While aspects herein are generally directed toward lateral pivot shift tests to determine injury to the ACL, those skilled in the art will appreciate how techniques cognizable under the disclosures herein can be applied in a variety of settings to perform and quantitatively analyze motion-based testing on patients.

The technology required to perform such testing can include inexpensive, widely-available consumer devices. Digital camera technology has been improving for over two decades, and is widely available in a variety of high-resolution products at low cost. These cameras can take video in a variety of formats, and with the assistance of file conversion and image processing software, can be used to collect and/or generate large amounts of data for analysis based on captured motion. This simple, accessible technology can be used to record the motion of human bodies to facilitate kinematic analysis and injury diagnosis.

For example, diagnosis of ACL injury according to the grading system described supra can be performed using digital camera technology. Video from the digital camera can be used to calculate lateral component translation, and various amounts of translation can be associated with injury grading. For example, in some patients and/or embodiments, increments between 1 and 10 millimeters (mm) of lateral compartment translation can define the pivot shift grade(s). It is to be appreciated that, while values can be described herein for increments, measurements, benchmarks, et cetera, such values are only provided for descriptive purposes and ease of understanding only. Those skilled in the art will appreciate that such values can vary significantly depending on, for example, practitioner, technique for administering a test, technique for quantifying test results, and other factors.

In order to accurately measure motion (e.g., lateral pivot shift) using video, markers can be affixed externally to the patient's skin in a noninvasive manner (or other tracking can be used, e.g., following bodily landmarks). While a variety of marking schemes can be supported by innovations herein, an example can include using circular stickers in a predetermined pattern. In an embodiment, the stickers can be affixed to bodily landmarks, such as bony protrusions. For example, in a lateral pivot shift test, three skin markers can be attached to bony landmarks on the lateral side of the knee joint. These bony landmarks can include Gerdy's tubercle, the fibular head, and the lateral epicondyle.

A digital camera can be positioned to capture motion of the markers and other aspects during a test. For example, in a pivot shift test, the video camera can record the lateral aspect of the knee during the pivot shift test. While a standard digital camera is disclosed herein, it is to be understood that most any image capture device (e.g., mobile phone, tablet, and others) can be employed without departing from the spirit and/or scope of the innovation.

Analysis (and/or processing) of the image capture (as described herein) can be accomplished in most any manner including, but not limited to using a mobile device "app" or "applet" or other suitable computing device. These and other variations of the innovation are to be included within the scope of this disclosure and claims appended hereto.

The video and/or image(s) can be processed into, for example, various coordinate systems in order to trace the markers and their motion in two or more dimensions. With respect to the lateral pivot shift test, the anteroposterior (AP) position of the femur can be calculated on consecutive still images extracted from the video recording. AP translation over time can be recorded and associated with various diagnoses.

Diagnoses relating to, for example, a lateral pivot shift test can be rendered by analysis of the reduction phase of the pivot shift. A sudden anterior translation of the distal femur can be associated with various grades or measurements indicative of ACL injury. In studies and/or embodiments, the sudden anterior translation of the lateral epicondyle can be on average 3.7±2.1 mm and occurred within 0.2±0.1 seconds from the start of such anterior translation. These shifts are successfully detected in accordance with disclosures herein, facilitating a simple and affordable method to evaluate the lateral pivot shift test.

Various tabulated and graphical quantifications of abnormal movement can be generated and/or presented and used to provide visual quantification of injury to practitioners. In embodiments, further analysis software can be employed to produce or validate an injury diagnosis based on such quantification.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, a portion of a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Markers, as described herein, are visible, noninvasive, external markings on a patient. Markers can include, but are not limited to, stickers, ink, and other identifiable visual features. Markers can be included in all shapes and sizes. For example, solid or outlined shapes such as circles, rectangles, triangles, and others can be affixed or drawn on bodily landmarks or arbitrary locations. In alternative examples, various lined, grid, or other patterns can be affixed or drawn. Markers can include various textures or finishes (e.g., reflective). Markers need not all be identical in every means cognizable in accordance with disclosures herein, and a plurality of shapes, sizes and techniques can be used in the same analysis. For example, a plurality of sticker markers can be attached to bodily landmarks, and a light source (e.g., laser) can project a grid over the body and affixed markers to provide additional scale and reference for analysis. These limited examples are intended only to suggest the spirit of this aspect, and do not define the breadth of possible marker configurations. Those skilled in the art will appreciate a wide variety of alternative markers or marking schemes that can be practiced in accordance with the spirit and scope of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

Turning now to FIG. 1, illustrated is a system 100 that processes images to render medical information. System 100 can include capture component 110 and processing component 120.

Capture component 110 can direct an image capture capability (e.g., video camera, still camera that collects a plurality of images) toward a target area (e.g., of a patient). Observation of the target area during a test (e.g., moving the target area through a range of motion to view abnormal motion, if any) can yield recordable information relating to an injury.

Capture component 110 can be embodied on or in a variety of devices. In some embodiments, capture component 110 is a standalone camera (e.g., digital video camera, digital still camera). In other embodiments, capture component 110 can be a camera or other suitable equipment within a phone (e.g., cellular telephone, smart phone), personal digital assistant, laptop computer, tablet, or other electronic device.

Processing component 120 can process data received from capture component 110 at least to render quantitative data relating to a test on a patient. In embodiments, processing component can determine quantities such as distance, angle, time, velocity, acceleration, and other measurements. Such measurements can be absolute (e.g., five millimeters) or relative (e.g., one-third of the distance between two known markers), and listed according to one or more units (e.g., millimeters) or in a unit-less form (e.g., according to an arbitrary coordinate system defined by at least processing component 120, according to relative measurements).

Capture component 110 can be configured to observe the motion of landmarks and/or a plurality of markers on a patient. In some embodiments, the camera can be substantially positioned at a predetermined distance and angle to enable calculations to be rendered in known units (e.g., camera remains static, in space or relative to patient).

In alternative or complementary embodiments, processing component 120 can be provided information that provides appropriate reference for the performance of calculations. For example, a practitioner can position capture component 110 one foot from a target area at an angle of 90 degrees to a surface defined by three or more markers. This information can be provided to processing component 120. Thereafter, capture component 110 can be positioned approximately one meter from the target at an angle of eight hundred mils to a surface defined by three or more markers. This information can be provided to processing component 120. In this way, processing component 120 can adjust processing to compensate for different distances and perspectives. As shown by this example, processing component 120 can further work in a plurality of different units, and easily convert between any commonly known unit (e.g., of distance, angle, time, velocity, acceleration, and others).

In another alternative or complementary embodiment, processing component 120 can determine parameters (e.g., distance and angle) relating capture component 110 to a target area based on information relating to the size and shape of markers. For example, a marker can be a circle, equilateral triangle, square, or other shape (e.g., including non-equilateral polygons) defined in terms of known units or spatial relationships. Processing component 120 can receive marker shape parameters and, based on the size and shape observed by capture component 110, calculate at least one scale to apply to the images.

In a detailed example of processing component 120 determining image parameters, a marker can be a circle with a diameter of one-half inch. With this information provided, processing component 120 can utilize images from capture component 110 (which, for example, may show the marker as an oval if the capture component does not view the marker straight-on) to determine an angle to the target and adjust calculations accordingly. Further, by being provided information (e.g., that the markers are one-half inch in diameter), a scale can be defined relative to the known-sized markers.

In still further alternative or complementary embodiments, a patient's information including measurements (e.g., length, width and height of joint structure) can be provided to define scales and/or coordinate systems, and/or to improve calculative accuracy and precision at least by comparison with other measured values.

In additional and/or combined embodiments, various range-finding techniques can be used to permit a device associated with at least capture component 110 to discern a distance from a target and/or markers. For example, lasers, sound, image recognition, and other techniques can be employed to accurately measure the distance between capture component 110 and at least a portion of the target without departing from the scope of the innovation.

Processing component 120 can view the changes between various times within a video and/or subsequent still images to define the motion of markers and/or the target area in terms of quantitative assessment. These results can be provided in tabulated form and/or displayed visually in terms of graphs or other visual depictions of the data. This quantitative data can be used to explicitly define abnormal motion in terms of measured changes, and thus be used in a diagnosis according to existing or derived criteria. Further, by defining the abnormal motion in terms of known quantities, subjective determinations of severity or grading can be validated or reevaluated.

In embodiments, capture component 110 and processing component 120 can be parts of a single device (e.g., physically connected within a common housing). In other embodiments, capture component 110 and processing component 120 can function at a distance. For example, capture component 110 and processing component 120 can operate remotely over a network (e.g., Internet, local area network, WiFi or cellular data network) using network adapters at least configure communication between capture component 110 and processing component 120. In other examples, capture component 110 and processing component 120 can utilize personal area networks or associated technologies such as BlueTooth™, infrared data association, near-field communication, and others. Those skilled in the art will appreciate various other means for communicating at a distance to facilitate sharing of information between capture component 110 and processing component 120.

Figure 2:
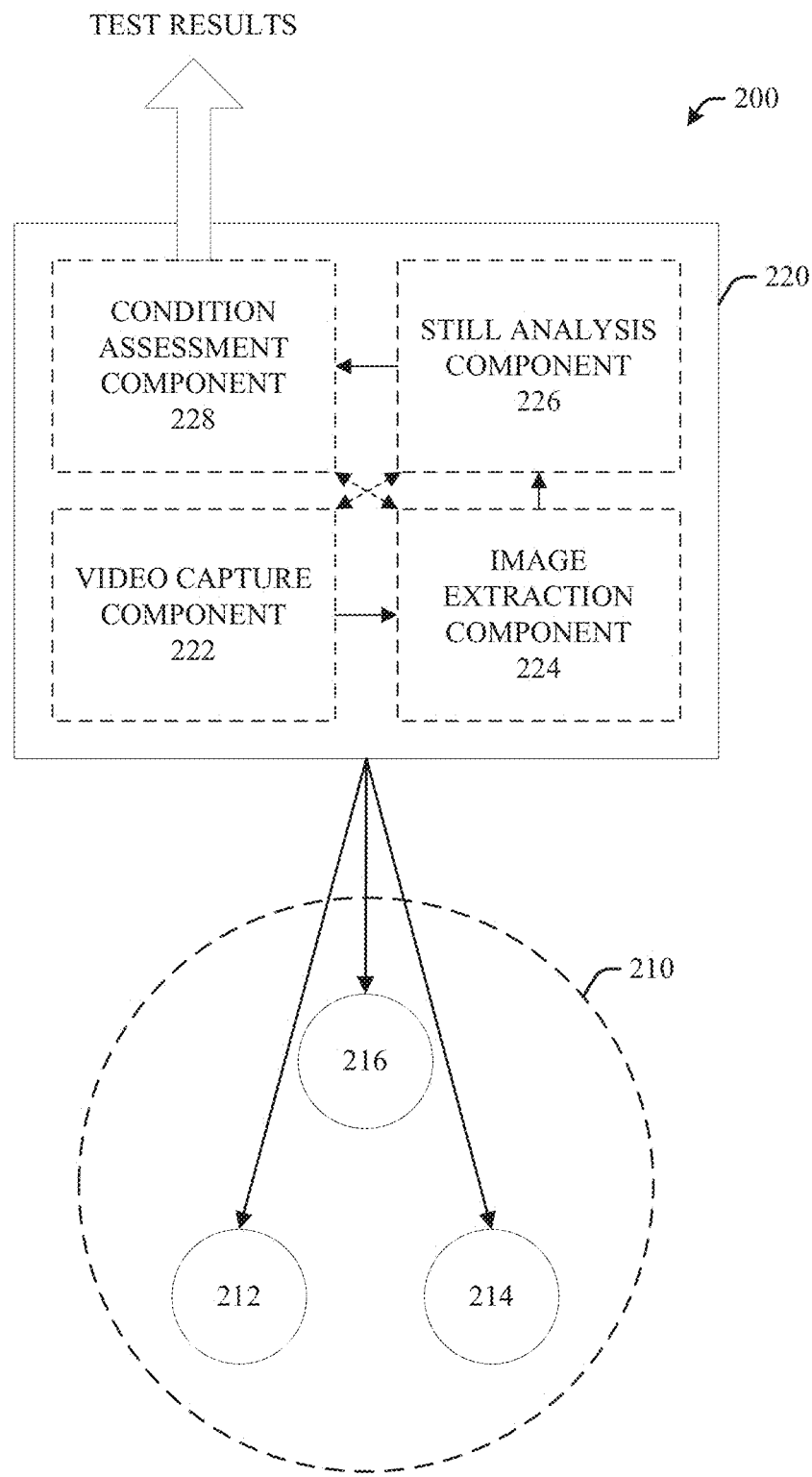
FIG. 2 illustrates a system that analyzes captured video to provide diagnosis relating to an injury.

Turning now to FIG. 2, illustrated is a system 200 that analyzes captured video to provide diagnosis relating to an injury. System 200 can include target area 210 and diagnostic module 220. While target area 210 is pictured in FIG. 2, this aspect is included only to facilitate understanding, and is not a required element to make systems or practice methods disclosed herein.

Target area 210 can be a patient joint, body part, or other area of a body which can be tested for injury by inducing movement. Target area 210 can further include a plurality of markers 212-214. While target area 210 and markers 212-214 are shown as circles, it is to be appreciated that this shape and configuration are one simple example intended to facilitate understanding, and that the vast number of possibilities for observed area and marker configuration are not treated exhaustively for purposes of brevity.

Diagnostic module 220 can be, but is not limited to, various combinations of software and/or hardware. In embodiments, diagnostic module 220 can include electronic devices including at least a camera capable of recording video. For example, diagnostic module 220 can include (but is not limited to) various computers (e.g., notebook, desktop, others), mobile devices (e.g., cellular telephone, smart phone, tablet, others), cameras (e.g., dedicated or integrated, with or without apps and/or wireless network connectivity), and other electronics, or combinations of two or more of such.

In alternative embodiments, diagnostic module 220 can be a software-only product that operates on a device including hardware such as the described above. In other or complementary embodiments, diagnostic module 220 can be a software package designed to run in any suitable computing environment that can access relevant information (e.g., video files) via one or more memories. While the hereafter generally directs the innovation toward a device including hardware for performing all aspects, those skilled in the art will appreciate how one or more aspects of diagnostic module 220 can be delivered exclusively as a software product that leverages other local and/or remote hardware to receive and process information for rendering test results based on patient motion.

Diagnostic module 220 can include or be operatively coupled to a source of video (e.g., video camera, storage receiving video, storage containing video). Video capture component 222 can be the source of video. While video capture component 222 is depicted as a sub-component of diagnostic module 220, it is to be appreciated that video capture component 222 can be a physically separate device. For example, video capture component 222 can be a dedicated (e.g., device primary function and identity is digital camera as compared with cameras integrated into other devices) external digital camera or device including a digital camera, or storage receiving or containing video (e.g., hard disk drive, solid state drive, secure digital card, universal serial bus drive, various read-only and random-access memory).

Diagnostic module 220 can further include image extraction component 224. Image extraction component 224 can extract and process video from video capture component 222 and render a product suitable for post-processing analysis. For example, image extraction component can perform (but need not perform all of, and is not limited to) cropping, zooming, stabilizing, adjusting color, adjusting brightness or contrast, superimposing additional aspects or information (e.g., grids, scales, frame numbers, text, indicators), time selection (e.g., editing video to shortest time period(s) when test performed), and others. Image extraction component 224 ultimately renders a plurality of frames that clearly and consistently depicts target area 210 and markers 212-216.

The plurality of frames from image extraction component 224 can be utilized by still analysis component 226 to quantify the motion depicted in the extracted image(s). In embodiments, still analysis component 226 can define and/or apply a coordinate system of at least 2 dimensions to the extracted image(s). With or without the coordinate system, still analysis component 226 can identify, measure, and tabulate changes between extracted image(s) in the position(s) of markers 212-216, and/or other identifiable features in target area 210.

Results from still analysis component 226 can be returned to condition assessment component 228. In some embodiments, condition assessment component 228 identifies abnormal motion related to at least one of markers 212-216 (or other identifiable features in target area 210) to render a diagnosis of injury. In alternative or complementary embodiments, condition assessment component 228 identifies a particular magnitude of movement related to at least one of markers 212-216 (or other identifiable features in target area 210) to determine a grade or severity of injury. Condition assessment component 228 can then return test results including a diagnosis (if any) related to the motion of target area 210 and markers 212-216 during a test on a patient.

Condition assessment component 228 can store results and use stored results or other statistics to adapt diagnoses according to previous test results. For example, patients exhibiting abnormal motion of similar magnitudes can be grouped together for statistical purposes and tracking of patient groups. Such statistical comparisons can increase the veracity of diagnoses and the function of diagnostic module 220.

Condition assessment component 228 can include or be provided information relating to symptoms of injury. For example, various magnitudes of AP shift can indicate ligamentous laxity and ACL injury. Condition assessment component 228 can include models or trends that can be matched to patient kinematics, quantitatively or qualitatively, to diagnose injury. In some embodiments, condition assessment component 228 can be provided one or more injuries to be tested, thus narrowing the number of possible models or trends to compare, thereby reducing the chance of inconclusive diagnoses.

Condition assessment component 228 can further be provided patient information (e.g., measurements related to target area and body) to adjust results based on patient physiology. For example, the absolute distance traveled by a limb in motion will be larger for an adult than a child. By providing details such as height, weight, reach, build, and so forth, condition assessment component 228 can improve the storage and grouping of test results, refine statistical analyses and/or comparisons performed, and specifically tailor a diagnosis to a unique patient.

To describe the functioning of diagnostic component 220, a non-limiting example is provided. Markers 212-216 are attached to target area 210 of a patient undergoing testing for abnormal motion indicative of injury. A video recording device, which can be video capture component 222 or another device, can be pointed at least to observe target area 210 to capture performance of the test on the patient, and record motion related to the test.

Video capture component 222 records, stores, and/or accesses video of the test. Thereafter, the video is provided to image extraction component 224. Image extraction component 224 identifies the portion of the video during which the test is performed (or a plurality of periods for repeated tests) and processes the image to provide a clear, stable, and consistent view (e.g., by stabilizing, cropping, converting to grayscale, adjusting brightness and contrast) for analysis. View consistency can be assured by maintaining a single reference view from frame-to-frame, ensuring differences in frames to be measured and/or analyzed are identifiable. As used herein, "optimizing" video can be a function of image extraction component 224 and involve performance of one or more of the functions described above, or others commonly associated with image or video optimization or improvement. Finally, image extraction component can provide the video as a series of still images. The still images can be associated with a time and/or other information relevant to the video.

In some embodiments, no enhancements are necessary (obviating at least one aspect of image extraction component 224), and video can be provided directly to still analysis component 226. In such embodiments, still analysis component 226 can view each frame within a video as a still, which need not be processed in any way before use by still analysis component 226.

Still analysis component 226 can identify and quantify the motion of markers 212-216 (and/or other aspects of target area 210) based on the differences between frames from a video. Various quantities, and tables or records thereof, can be generated based on a plurality of frames. The records of recorded quantities can be presented visually and used in calculations to refine the data relating to the test on the patient.

After still analysis component 226 quantifies the motions recorded in a video or portions thereof, results can be provided to condition assessment component 228. Condition assessment component 228 can identify abnormal motion using the quantities (e.g., by analyzing the difference between consecutive or groups of quantities). For example, in a lateral pivot shift test, motion can be tracked according to markers which display a smooth curve during the test until a sudden AP shift, which can be identified by condition assessment component 228 to diagnose rotational instability indicating ACL damage. Depending on the magnitude of the abnormal AP shift, the ACL damage can be graded or otherwise represented in terms of severity. In this way, diagnoses can be rendered by condition assessment component 228.

Figure 3:
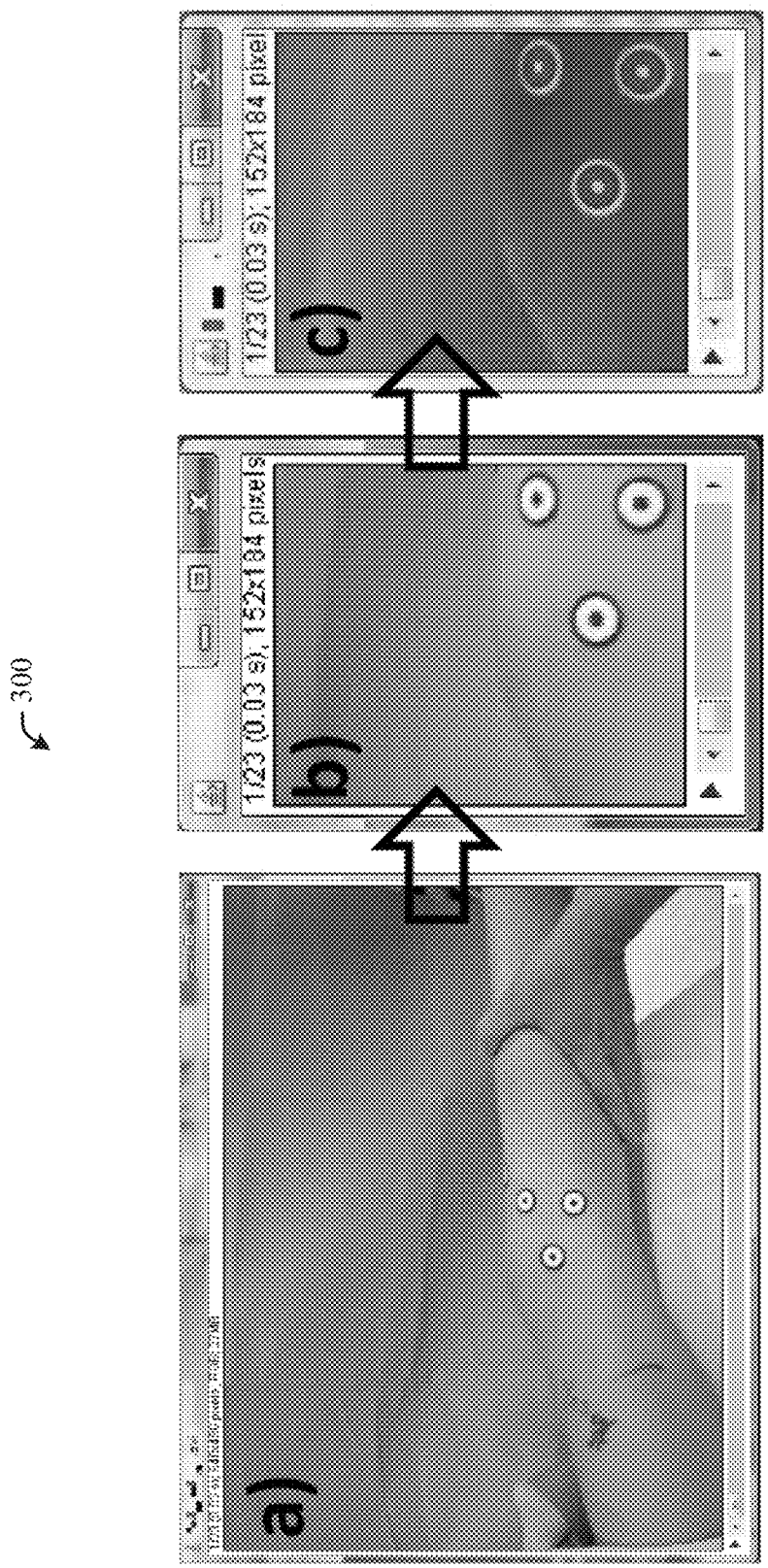
FIG. 3 illustrates is an example diagram of techniques described herein as applied to a lateral pivot shift test for diagnosing ACL injury.

Turning now to FIG. 3, illustrated is an example diagram 300 of techniques described herein as applied to a lateral pivot shift test for diagnosing ACL injury. A particular combination of aspects is shown in example diagram 300, but these aspects are intended to be non-limiting and provide additional context for techniques described herein.

In the example, as shown in FIG. 3, ring-shaped white stickers (i.e., 14 mm in diameter and commonly available in office supply stores) can be attached as skin markers on bony landmarks of a patient knee. In example diagram 300, the stickers function as markers for the lateral epicondyle, Gerdy's tubercle and the fibular head. The distance between the centers of the markers located over Gerdy's tubercle and the fibular head can be preliminarily measured by a test administrator using a ruler or other appropriate device. In some embodiments, measurements can be taken automatically or estimated as described herein.

A pivot shift test can be performed in a standardized manner. In some embodiments, various systems or methods herein can include various aspects to train (e.g., demonstrate a standard technique, guide through technique) a practitioner to use a standardized manner in accordance with standards and/or formats used by information libraries available to hardware and/or software for performing techniques herein. In alternative or complementary embodiments, a practitioner can select a manner in which to perform a pivot shift test, thereby configuring systems and methods in accordance with the herein to best represent how the particular practitioner performs the technique. In still further alternative or complementary embodiments, systems and methods can be trained to a particular practitioner or technique based on a plurality of testing results over time.

A video recording can be taken of at least the lateral aspect of the knee during a pivot shift test using a digital camera (e.g., commonly available in stores carrying electronic devices). In embodiments, the lateral aspect of the knee (or other target area) can have a background including, and/or be partially covered by, a monotone sheet or other uniform colors/patterns to improve processing and reduce noise.

The video recording (e.g., of a pivot shift test, aspects of which are shown in FIG. 3) can be reformatted (e.g., from a proprietary format to audio-video interleave container format) to one or more file types or standards for use in image processing software. The video recording can be trimmed to have one sequence of a test (e.g., one iteration of a pivot shift test) and the iteration can be analyzed using image processing software. Various free or commercial image processing packages can be employed (e.g., National Institute of Health Image J) to process one or more portions of the video recording and/or individual still frames therefrom.

For example, the video recording (in its original form or reformatted) can be opened as a stack of images by image processing software (e.g., one image from the stack as in FIG. 3a). The images can be cropped to capture only the three markers within the imaging frames throughout the test (e.g., as in FIG. 3b). In the example, color information of the images can be converted to 8-bit grayscale, and the brightness and contrast can be adjusted to highlight the skin markers. The areas of the skin markers are selected by the area detection tool by the level of grayscale. The detecting threshold of the grayscale level can be adjusted to maximize the areas of the markers and to minimize the unwanted area selection (e.g., as in FIG. 3c). It is to be appreciated that additional aspects can be performed in image processing, and image processing need not include every aspect described above.

Figure 4:
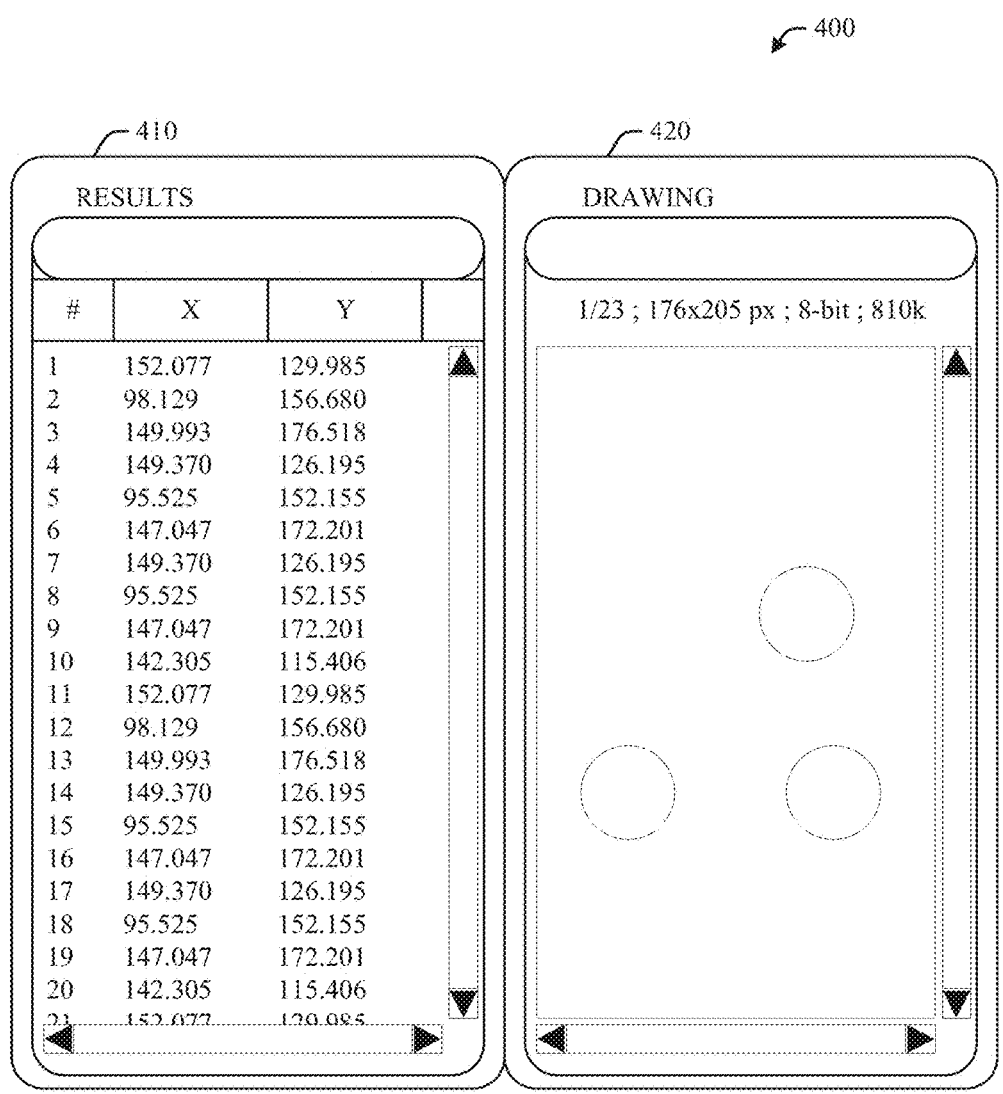
FIG. 4 illustrates an example interface showing the XY plots of the centroid for the detected areas in both numerical and graphical forms.

With reference now to FIG. 4, illustrated is an example interface 400 showing the XY plots of the centroid for the detected areas. The outlines of detected area can be provided after conducting, for example, particle analysis. Tabulated XY plots 410 of the centroids are used to calculate the a-p translation of the lateral compartment. Outline data 420 facilitates identification of each detected skin marker-area and the corresponding XY plot of its centroid location. (420 and FIG. 5)

Figure 5:
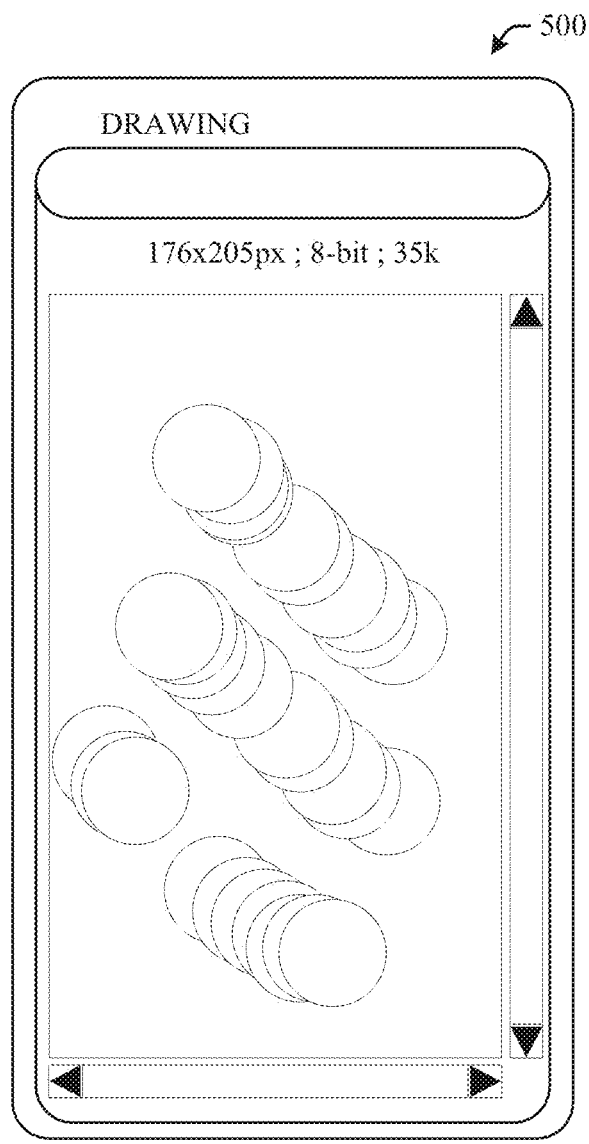
FIG. 5 illustrates a portion of an example interface showing a plurality of markers plotted over a period of time.

FIG. 5 illustrates plot window 500 depicting a plurality of plots relating to a range of motion for three markers, corresponding to outline data 420. In this way, a video or series of frames can be viewed through a period of time (e.g., iteration of a motion-based test on a patient) in a single snapshot. In embodiments, plot window 500 can include various other aspects such as highlighting or noting extremes or irregularities (e.g., maximum or minimum translation in a particular direction, absolute maximum or minimum translation, detection of abnormal motion or motion that does not conform to curves).

Figure 6:
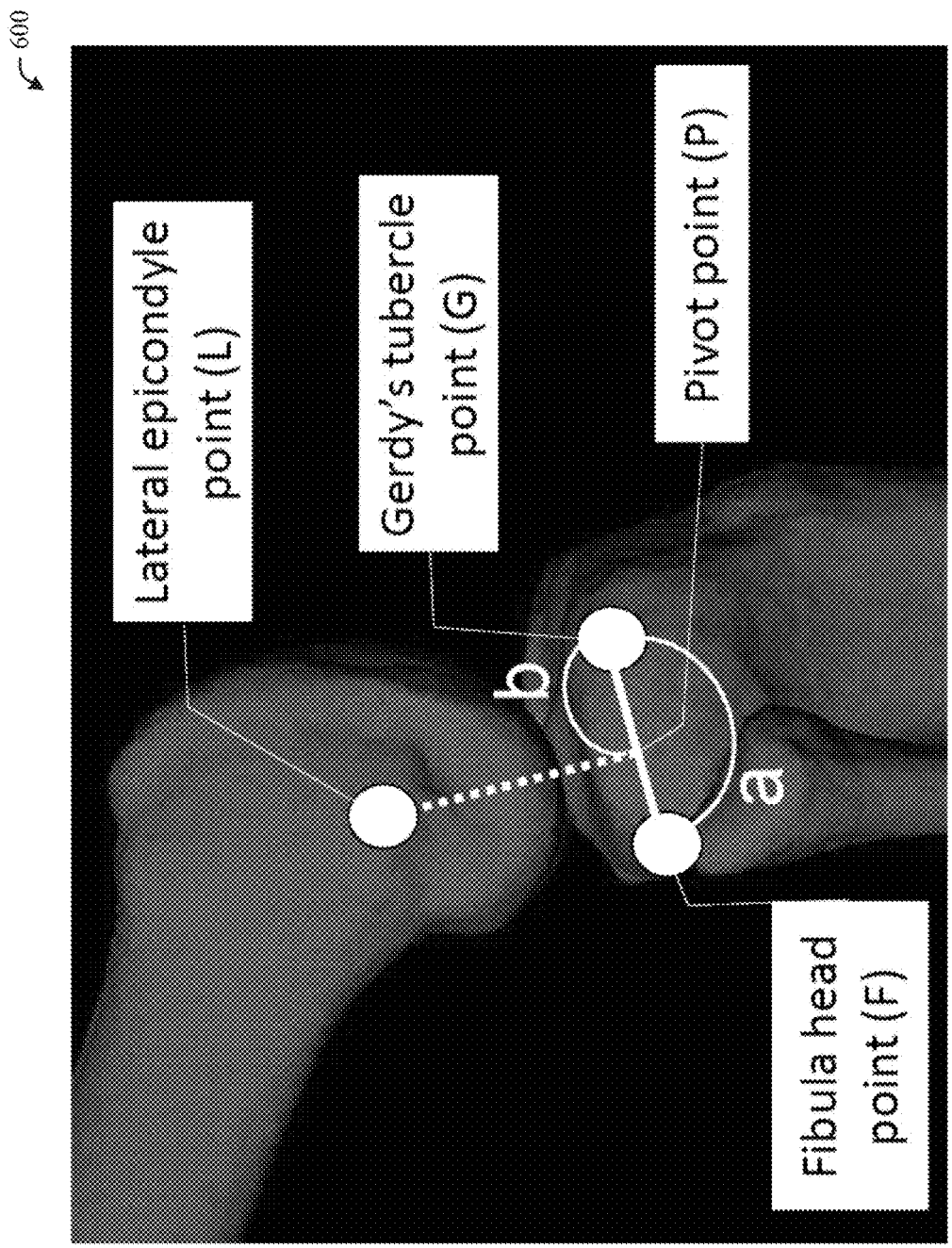
FIG. 6 illustrates a representation of anatomical aspects used to calculate lateral compartment translation.

Turning now to FIG. 6, illustrated is a representation 600 of anatomical aspects used to calculate lateral compartment translation. In each frame of a video, the XY plot of the intersection point can be termed as "pivot point (P)" between the tibial horizontal line. The tibial horizontal line can be defined by a line connecting the centroids of Gerdy's tubercle (G) and fibular head markers (F), and a perpendicular line from the centroid of the lateral epicondyle marker (L) to the tibial horizontal line. The ratio of the perpendicular offset length of the lateral epicondyle point from the Gerdy's tubercle point (distance "b" in FIG. 6) to the length of the tibial horizontal line (distance "a" in FIG. 6) is calculated from the XY plot data. The femoral AP position from Gerdy's point can be calculated by multiplying the ratio by the distance of the two tibial points.

In ACLs, using calculative aspects such as those described supra, lateral compartment translation during a pivot shift test can vary between 1 mm and 15 mm, whereas actual bony movement (e.g., posterior tibial translation) can (but need not) be substantially larger (e.g., up to 30 mm). Values can be smaller than the actual bony movement in some embodiments, but lateral compartment translation can be consistently observed in accordance with the techniques herein. Other averages or quantitative values can be observed in various embodiments and with different techniques applied to the ACL or other patient parts. As noted supra, specific values provided herein are intended for descriptive purposes only, may vary significantly depending on testing factors, and should in no way be interpreted as limiting in lieu of express language to the contrary.

Figure 7:
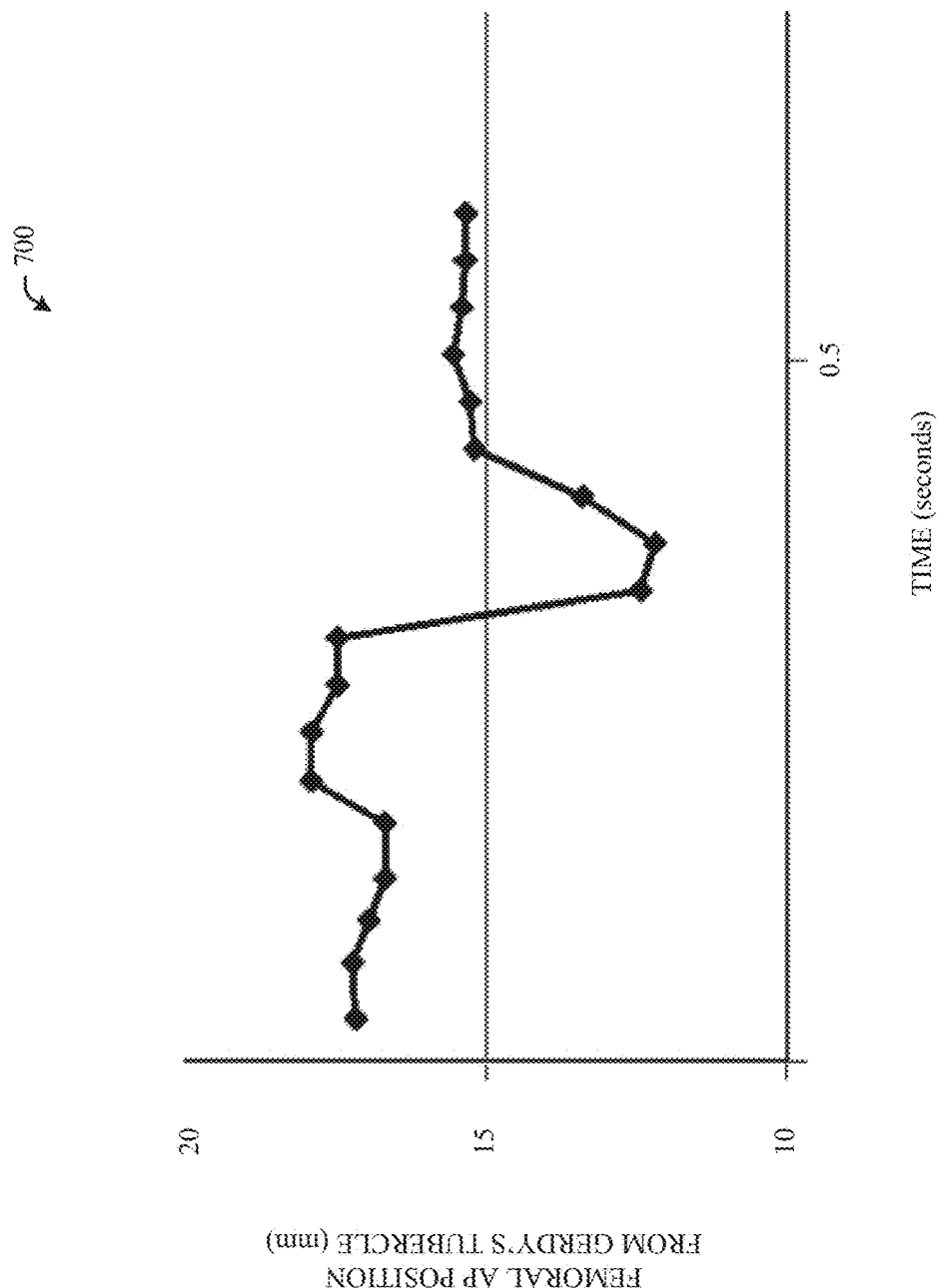
FIG. 7 illustrates a sample graph plotting time against femoral AP position from Gerdy's tubercle in millimeters during a pivot shift test.

Turning now to FIG. 7, illustrated is a sample graph 700 plotting time against femoral AP position from Gerdy's tubercle in millimeters during a pivot shift test. The femoral AP position from the Gerdy's point can suddenly decrease in ACL deficient knees during the reduction phase of the pivot shift test, while the contralateral intact knees did not demonstrate such anteroposterior shift. For example, in embodiments such as that represented by sample graph 700, the sudden decrease can have average values of approximately 3.7±2.1 mm, with values as large as 6.4 mm or as small as 1.5 mm. The anterior translation of the distal femur relative to the tibia can occur at roughly the same time for tests performed in a standardized manner. For example, in sample graph 700, translation can occur within 0.2±0.1 seconds. As set forth above, and as will be appreciated by skilled practitioners, such values are set forth for descriptive purposes only.

Sample graph 700 describes how lateral compartment translation during a pivot shift test in the ACL deficient knee can be consistently observed and quantitatively measured using image analysis techniques as set forth herein. Standard digital camera systems and image processing software (including software available free of charge) quantify sudden anterior translation of the lateral compartment during the reduction phase of the lateral pivot shift test. Lateral pivot shift can be been described as "forward subluxation of the lateral tibial plateau on the femoral condyle and its spontaneous reduction." (Galway, et al. (1972) Pivot shift: a clinical sign of symptomatic anterior cruciate deficiency. J Bone Join Surg Br 54-B:763-764.) The a-p translation in the lateral compartment can be reflected in clinical grading of the pivot shift test. Tracking of skin motion in this study can be facilitated by separate, non-invasive markers on distal femur and proximal tibia. The different directional skin motion of bony landmarks on distal femur and proximal tibia can be detected by dynamic video motion image analysis.

In view of the exemplary systems and other aspects described supra, methodologies that may be implemented in accordance with the disclosed subject matter can be described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers. The term article of manufacture, as used herein, is intended to encompass a computer program accessible from any computer-readable device, carrier, or media.

Figure 8:
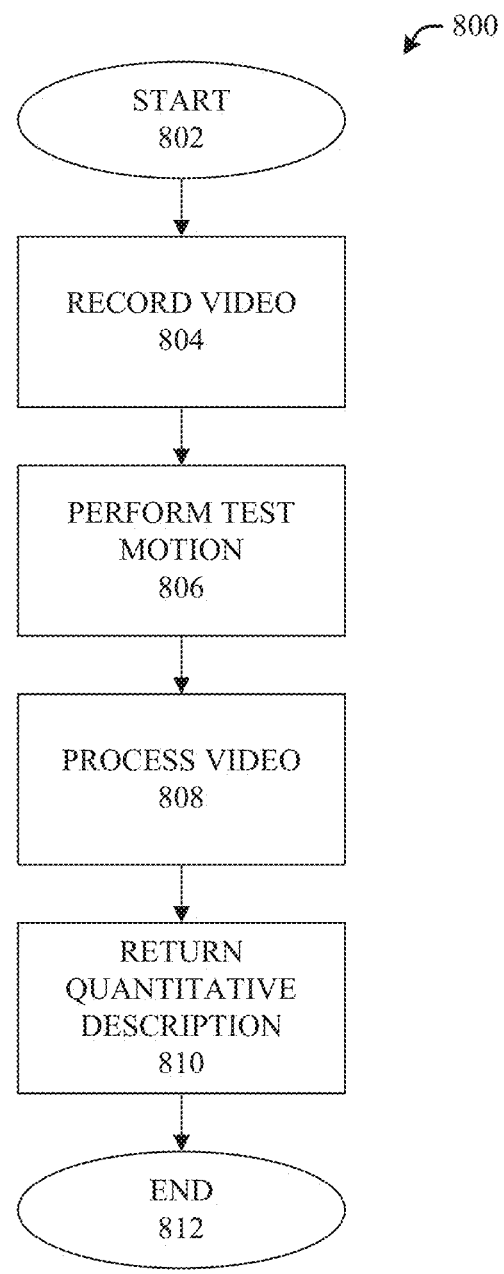
FIG. 8 illustrates a sample methodology that describes the results of a test involving motion of a patient part in terms of quantitative information.

Turning now to FIG. 8, illustrated is a sample methodology 800 that describes the results of a test involving motion of a patient part in terms of quantitative information. Methodology 800 can start at 802 and proceed to 804 where a video recording can be triggered. At 806, a test motion can be performed that is captured on the video recording. For example, the test performed at 806 can be a pivot shift test on a patient leg to determine ligamentous laxity symptomatic of ACL damage. The video of the test can be stored for analysis.

At 808, the video of the test can be processed. Processing at 808 can include, but is not limited to, various image processing to enhance or modify the video for analysis, as well as the analysis itself. At either 808 or 810, quantitative data describing numerically the motion of one or more areas of interest related to the test at 806 can be discerned from the video. At 810, the quantitative values associated with the bodily motion through the test can be returned, for manual or automatic analysis. Thus, rather than relying on individual judgment or estimates, specific quantities relating to displacement can be used to describe both normal and abnormal motion to facilitate diagnoses, prognoses, and other details relating to a potential medical condition.

Figure 9:
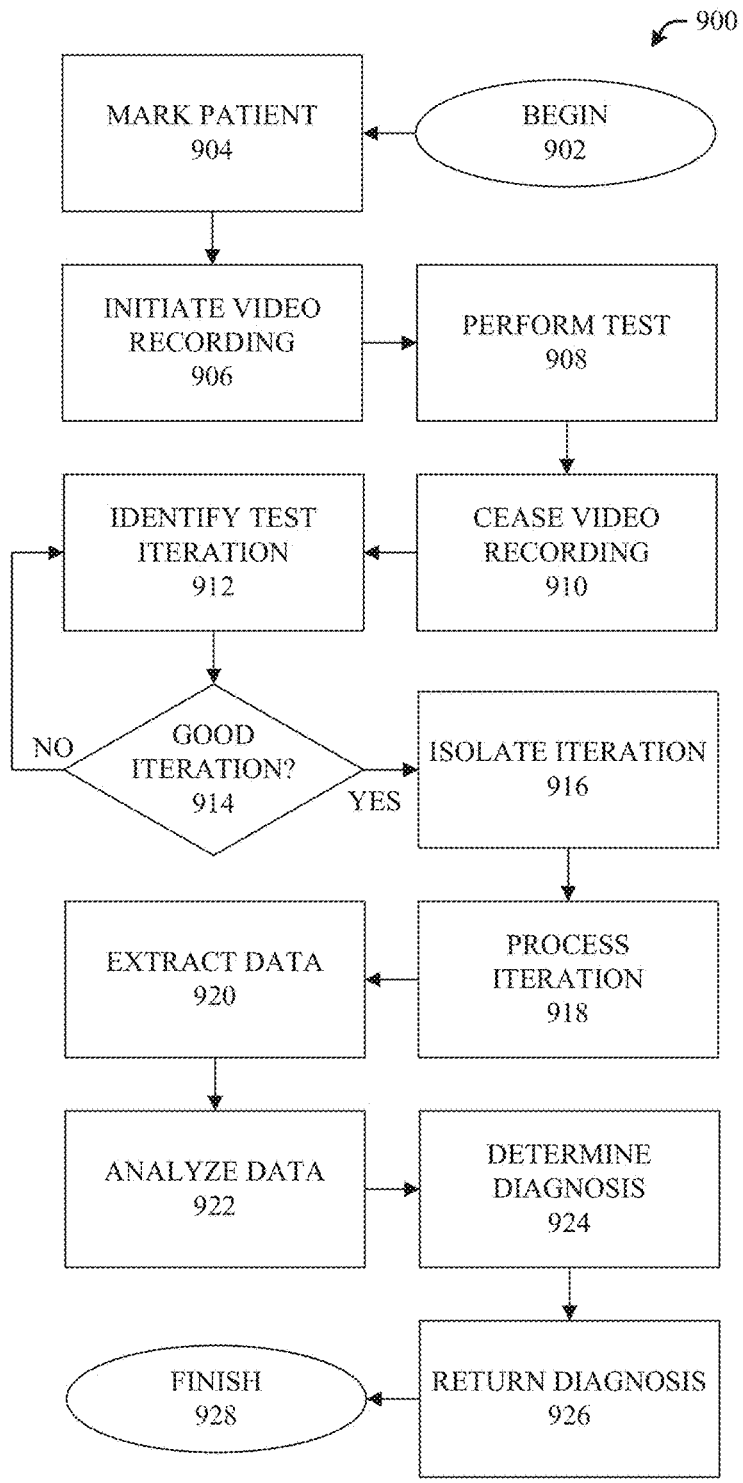
FIG. 9 illustrates a sample methodology that diagnoses a medical condition based on a test recorded to video.

Turning now to FIG. 9, illustrated is a sample methodology 900 that diagnoses a medical condition based on a test recorded to video. At 902, methodology 900 begins and proceeds to patient marking at 904. Patient marking at 904 can include affixing or applying non-invasive indicators to the patient that can be identified and tracked by image processing software. In embodiments, markers can be applied to bony landmarks such as on Gerdy's tubercle, the fibula head and the lateral epicondyle of the knee.

After the patient has been marked, a video recording can be initiated at 906. With the video recording underway, a test causing motion of the markers can be performed at 908. In embodiments, the test can be a lateral pivot shift test performed on a patient knee to determine whether injury to the ACL may exist. In embodiments, the test at 908 can be performed a plurality of times resulting in several iterations of the test motion.

After completing all desired iterations of the test at 908, video recording can cease at 910. The video can be stored and methodology 900 can proceed to 912 where an iteration of the test performed at 908 is identified. In embodiments, software can be used to automatically identify one or more iterations at 912.

At 914, a determination is made as to whether an identified iteration is a "good" iteration. A good iteration can be determined based on the presence of an unobstructed view of the markers, high resolution, easily detectable motion, and others. If the iteration identified at 912 is of poor quality (e.g., obstructions, blurring, extreme camera movement), methodology 900 can recycle to 912 where another iteration is identified and evaluated at 914. In embodiments, a best iteration can be selected for analysis among a plurality of iterations. If the determination at 914 returns a signal of a good iteration (or the best iteration), methodology 900 can proceed to 916.

At 916, the iteration approved at 914 is isolated for processing. For example, the video being used can be trimmed to only include the desired iteration. In embodiments, isolation of one or more iterations can occur between 912 and 914 or otherwise before a good iteration is confirmed at 914. In embodiments, a plurality of iterations can be isolated for individual analysis, either for one patient and/or test, or for use in conjunction with a plurality of patients and/or tests. Parallel or a plurality of results (as described throughout) for multiple iterations can be generated for statistical analysis, to improve result veracity, and other purposes.

After isolating an iteration at 916, the isolated iteration can be processed at 918. Iteration processing at 918 can include, but is not limited to, enhancement of one or more video clips and/or images associated with the iteration. For example, a video can be stabilized and/or cropped, have its color adjusted, have its brightness and/or contrast adjusted, be zoomed or scaled, and have other techniques performed to optimize view and identification of at least the markers against the patient and background.

At 920, using a uniform video file or series of images (e.g., that can be enhanced at 918), data relating to the test can be extracted. Data extracted can include, but is not limited to, information relating to time and space during a test iteration. Quantities such as distance, angle, speed, acceleration, and others, can be recorded and/or calculated with respect to the test based on changes during the video (or between consecutive images). These quantities can be applied to a coordinate system of two or more dimensions, and associated with particular points in time and/or extracted images. Tabulation of quantitative movement data at 920 facilitates its analysis at 922.

At 922, data can be analyzed. Various derived quantities can be discerned and coupled with the raw data recorded at 920. Information such as derivatives can be used to detect abnormalities or sudden changes that can be used in diagnoses. For example, in a pivot shift test, a sudden displacement can be identified.

After analysis at 922 is complete, methodology 900 can proceed to 924 where a diagnosis is determined. The diagnosis at 924 can employ results of the analysis at 922 to determine a (or at least suggest a preliminary) diagnosis. In embodiments, various possible quantities determined between 920 and 924 can be associated with injury or other condition. In embodiments, such quantities can be ranges. For example, to provide a graded diagnosis to ACL injury, a predetermined quantity or quantities of sudden displacement can be associated with a degree of injury. If no sudden pivot shift occurs, the diagnosis is negative and no injury is detected. If any abnormal pivot shift occurs less than a first threshold, a mild (e.g., Grade I) diagnosis is assigned. If abnormal pivot shift between the first threshold and a second threshold occurs, a moderate (e.g., Grade II) diagnosis is assigned. For abnormal pivot shift greater than the second threshold, a severe (e.g., Grade III) diagnosis can be assigned.

In alternative embodiments, no grade is provided, but rather one or more measurements quantifying abnormal motion are provided. In embodiments, methodology 900 can be trained (e.g., based on a statistical set, based on ongoing results) to vary its diagnoses based on an ongoing series of tests and/or user input. Such embodiments provide a complementary configuration or alternative to embodiments that exclusively employ fixed, predetermined values to represent various conditions.

After a diagnosis is determined, the diagnosis and any further relevant information are returned at 926. Thus, one or more entities associated with methodology 900 can receive a diagnosis based on analysis of a video of test performance. Methodology 900 finishes at 928 following return of the diagnosis.

As noted supra, the accuracy, precision, and customization of digital analysis can be improved and refined by integrating larger, statistically-relevant patient groups into systems and methods described herein. For example, disparity between skin movement and actual translation of the bones comprising the lateral compartment can be reduced and/or refined, especially in patients with a larger body habitus. Nonetheless, even in individual patients, sudden shift of the lateral compartment of the knee joint can be successfully detected by this video-based image analysis measurement method.

In a related aspect, a "brace" or rig can be designed to free clinician's hands to perform the pivot shift test and establish a consistent and/or appropriate distance and/or angle from a target area and markers for the video capture. It will be appreciated appreciated that such a brace can also make the pivot shift test more feasible in the field (e.g., on-sight at athletic event).

In various embodiments, the brace can include a mounting point and one or more camera mounting rods that can set various cameras or devices at a predetermined distance and/or angle. In embodiments, a mounting rod can telescope and/or change angles for use in a variety of settings, and software used in conjunction with the video recorded can adjust for a particular distance or angle. In embodiments, the brace and mounting equipment are not directly attached to one another, but instead attached to a fixed third point or component that ensures a consistent frame of reference for performance and recording of the test.

The brace can include support for degrees of freedom that can benefit from restriction (e.g., beyond the scope of performance of a test, facilitating wearer's motion without risking additional injury). In embodiments, the brace can lock when not in use to support and protect a potentially injured body part. The brace can (but need not) include various "grip points" and/or pivots designed to improve the uniformity and efficiency of practitioners performing a test on the body part. Various embodiments of a brace as set forth herein can be made for various parts of the body (e.g., knee, elbow, ankle) and in various sizes (e.g., small for children, large for adult). Further, various embodiments of a brace can allow the brace to be adjusted to multiple sizes. This brace or rig design is to be included within the scope of this disclosure and claims.

Figure 10:
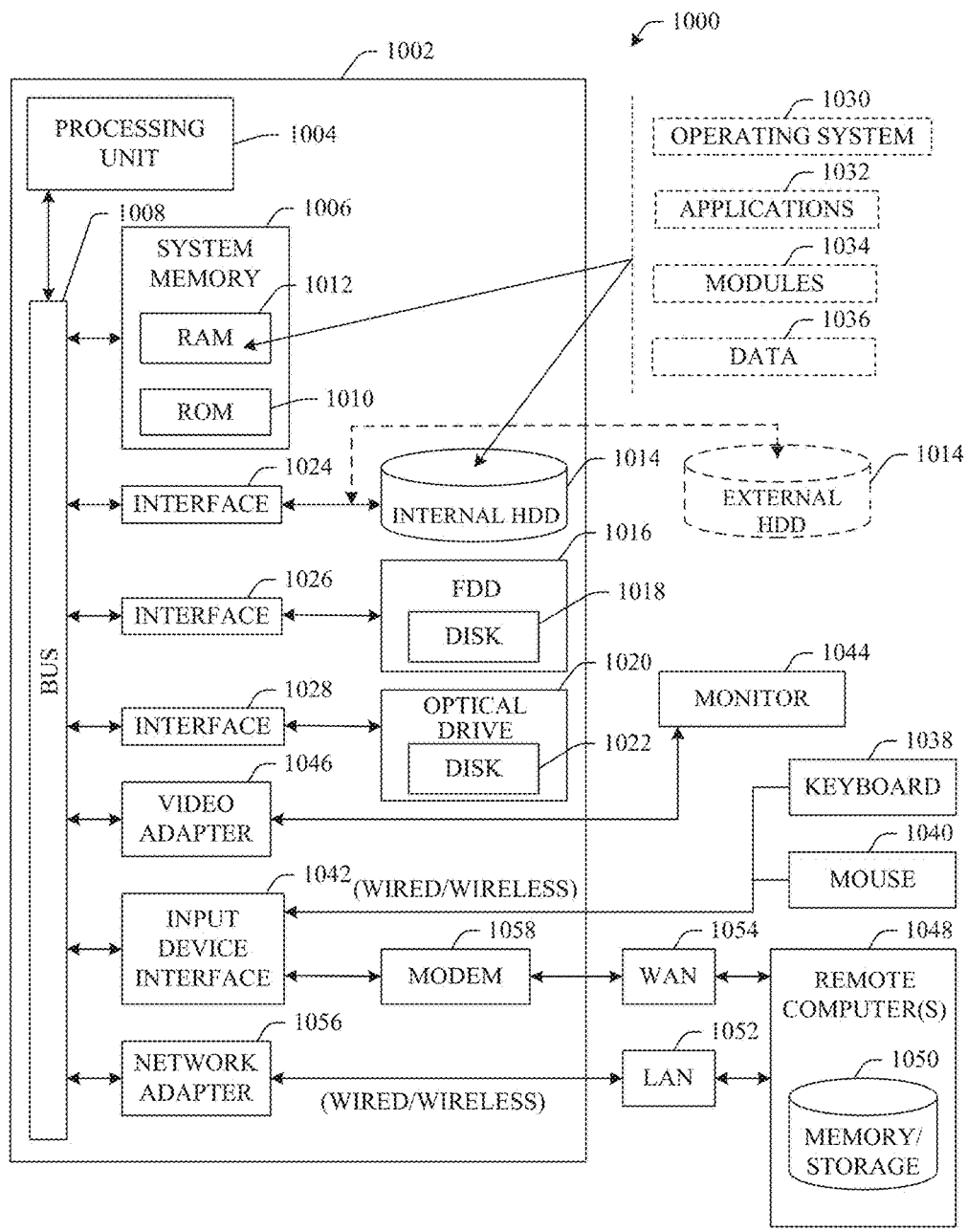
FIG. 10 illustrates a brief general description of a suitable computing environment wherein the various aspects of the subject innovation can be implemented.

FIG. 10 illustrates a brief general description of a suitable computing environment wherein the various aspects of the subject innovation can be implemented.

Figure 11:
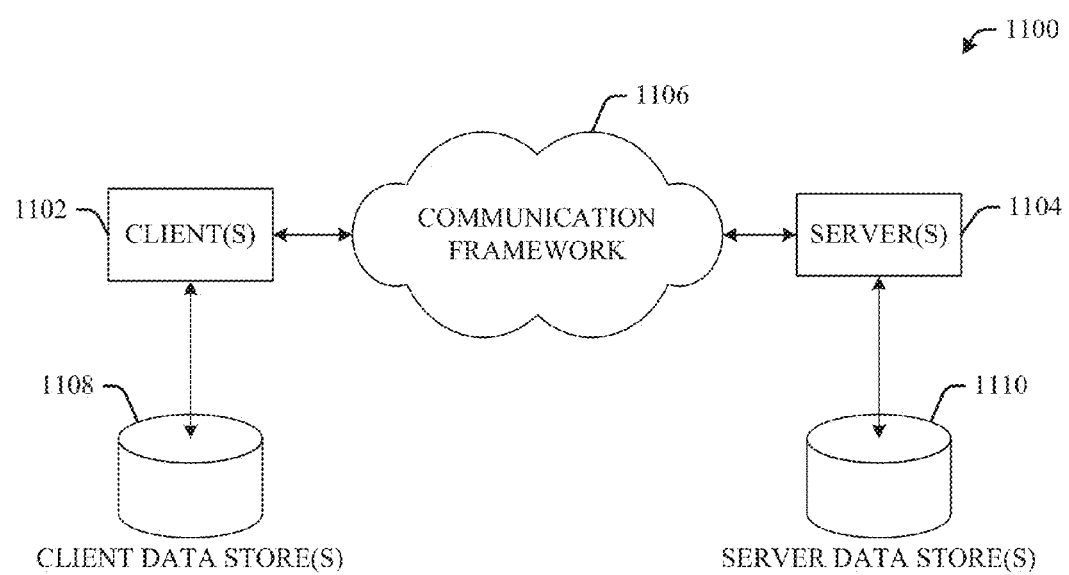
FIG. 11 illustrates a schematic diagram of a client-server computing environment wherein the various aspects of the subject innovation can be implemented.

FIG. 11 illustrates a schematic diagram of a client—server-computing environment wherein the various aspects of the subject innovation can be implemented.

With reference to FIG. 10, the exemplary environment 1000 for implementing various aspects of the innovation includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures may also be employed as the processing unit 1004.

The system bus 1008 can be any of several types of bus structure that may further interconnect to a memory bus (with or without a memory controller), a peripheral bus, and a local bus using any of a variety of commercially available bus architectures. The system memory 1006 includes read-only memory (ROM) 1010 and random access memory (RAM) 1012. A basic input/output system (BIOS) is stored in a non-volatile memory 1010 such as ROM, EPROM, EEPROM, which BIOS contains the basic routines that help to transfer information between elements within the computer 1002, such as during start-up. The RAM 1012 can also include a high-speed RAM such as static RAM for caching data.

The computer 1002 further includes an internal hard disk drive (HDD) 1014 (e.g., EIDE, SATA). Alternatively or in addition, an external hard disk drive 1015 may also be configured for external use in a suitable chassis (not shown), a magnetic disk drive, depicted as a floppy disk drive (FDD) 1016, (e.g., to read from or write to a removable diskette 1018) and an optical disk drive 1020, (e.g., reading a CD-ROM disk 1022 or, to read from or write to other high capacity optical media such as the DVD). The hard disk drives 1014, 1015 magnetic disk drive 1016 and optical disk drive 1020 can be connected to the system bus 1008 by a hard disk drive interface 1024, a magnetic disk drive interface 1026 and an optical drive interface 1028, respectively. The interface 1024 for external drive implementations can include Universal Serial Bus (USB), IEEE 1394 interface technologies, and/or other external drive connection technologies.

The drives and their associated computer-readable media provide nonvolatile storage of data, data structures, computer-executable instructions, and so forth. For the computer 1002, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and system memory 1006, including an operating system 1030, one or more application programs 1032, other program modules 1034 and program data 1036. All or portions of the operating system, applications, modules, and/or data can also be cached in the RAM 1012. It is appreciated that the innovation can be implemented with various commercially available operating systems or combinations of operating systems.

A user can enter commands and information into the computer 1002 through one or more wired/wireless input devices, e.g., a keyboard 1038 and a pointing device, such as a mouse 1040. Other input devices (not shown) may include a microphone, an IR remote control, a joystick, a game pad, a stylus pen, touch screen, or the like. These and other input devices are often connected to the processing unit 1004 through an input device interface 1042 that is coupled to the system bus 1008, but can be connected by other interfaces, such as a parallel port, an IEEE 1394 serial port, a game port, a USB port, an IR interface, etc.

A monitor 1044 or other type of display device is also connected to the system bus 1008 via an interface, such as a video adapter 1046. In addition to the monitor 1044, a computer typically includes other peripheral output devices (not shown), such as speakers, printers, etc.

The computer 1002 may operate in a networked environment using logical connections via wired and/or wireless communications to one or more remote computers, depicted as remote computer(s) 1048. The remote computer(s) 1048 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1050 is illustrated. The logical connections depicted include wired/wireless connectivity to a local area network (LAN) 1052 and/or larger networks, e.g., a wide area network (WAN) 1054. Such LAN and WAN networking environments are commonplace in offices and companies, and facilitate enterprise-wide computer networks, such as intranets, all of which may connect to a global communications network, e.g., the Internet.

When used in a LAN networking environment, the computer 1002 is connected to the local network 1052 through a wired and/or wireless communication network interface or adapter 1056. The adapter 1056 may facilitate wired or wireless communication to the LAN 1052, which may also include a wireless access point disposed thereon for communicating with the wireless adapter 1056.

When used in a WAN networking environment, the computer 1002 can include a modem 1058, or is connected to a communications server on the WAN 1054, or has other means for establishing communications over the WAN 1054, such as by way of the Internet. The modem 1058, which can be internal or external and a wired or wireless device, is connected to the system bus 1008 via the serial port interface 1042 as depicted. It should be appreciated that the modem 1058 can be connected via a USB connection, a PCMCIA connection, or another connection protocol. In a networked environment, program modules depicted relative to the computer 1002, or portions thereof, can be stored in the remote memory/storage device 1050. It will be appreciated that the network connections shown are exemplary and other means of establishing a communications link between the computers can be used.

The computer 1002 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet).

FIG. 11 is a schematic block diagram of a sample-computing environment 1100 that can be employed for practicing aspects of the afore-mentioned methodology. The system 1100 includes one or more client(s) 1102. The client(s) 1102 can be hardware and/or software (e.g., threads, processes, computing devices). The system 1100 also includes one or more server(s) 1104. The server(s) 1104 can also be hardware and/or software (e.g., threads, processes, computing devices). The servers 1104 can house threads to perform transformations by employing the components described herein, for example. One possible communication between a client 1102 and a server 1104 may be in the form of a data packet adapted to be transmitted between two or more computer processes. The system 1100 includes a communication framework 1106 that can be employed to facilitate communications between the client(s) 1102 and the server(s) 1104. The client(s) 1102 are operatively connected to one or more client data store(s) 1108 that can be employed to store information local to the client(s) 1102. Similarly, the server(s) 1104 are operatively connected to one or more server data store(s) 1110 that can be employed to store information local to the servers 1104.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects. In this regard, it will also be recognized that the various aspects include a system as well as a computer-readable medium having computer-executable instructions for performing the acts and/or events of the various methods.

In addition, while a particular feature may have been disclosed with respect to only one of several implementations, such feature may be combined with one or more other features of the other implementations as may be desired and advantageous for any given or particular application. To the extent that the terms "includes," and "including" and variants thereof are used in either the detailed description or the claims, these terms are intended to be inclusive in a manner similar to the term "comprising." Furthermore, the term "or" as used in either the detailed description of the claims is meant to be a non-exclusive "or".

Furthermore, as will be appreciated, various portions of the disclosed systems and methods may include or consist of artificial intelligence, machine learning, or knowledge or rule based components, sub-components, processes, means, methodologies, or mechanisms (e.g., support vector machines, neural networks, expert systems, Bayesian belief networks, fuzzy logic, data fusion engines, classifiers . . . ). Such components, inter alia, can automate certain mechanisms or processes performed thereby to make portions of the systems and methods more adaptive as well as efficient and intelligent.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

It should be appreciated that any patent, publication, or other disclosure material, in whole or in part, that is said to be incorporated by reference herein (or otherwise applied) is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

What is claimed is:

1. A method that quantifies a medical condition based on a bodily motion, comprising:
   performing a pivot shift test related to three identifiable points of a knee of a patient, wherein the three identifiable points include a first point located at a Gerdy's tubercle of the patient, a second point located at a fibular head of the patient, and a third point located at a lateral epicondyle of a femur of the patient;
   recording performance of the pivot shift test in a plurality of frames;
   determining a plurality of quantities based on the three identifiable points from consecutive frames among the plurality of frames, wherein each of the quantities is a femoral anteroposterior position from Gerdy's point of the femur that is determined from a respective one of the consecutive frames and that is calculated by (i) determining a pivot point for the respective one of the consecutive frames, wherein the pivot point is a point where a first line from the first point intersects a second line between the second point and the third point, with the first line being perpendicular to the second line, (ii) determining a first linear distance from the third point to the pivot point for the respective one of the consecutive frames, (iii) determining a second linear distance from the second point to the third point for the respective one of the consecutive frames, (iv) determining a ratio of the first linear distance to the second linear distance for the respective one of the consecutive frames, and (v) determining the quantity for the respective one of the consecutive frames based on the ratio;
   determining that a medical condition exists based on a plurality of the quantities; and
   generating at least one of a tabulated or graphical quantification of abnormal movement based on the quantities, wherein the at least one of the tabulated or graphical quantification of abnormal movement facilitates assigning a grade to the medical condition based at least in part on a magnitude based on one or more of the quantities satisfying a predetermined condition associated with a degree of movement.

2. The method of claim 1, further comprising marking the three identifiable points.

3. The method of claim 1, wherein the determining the plurality of quantities is conducted according to a coordinate system.

4. The method of claim 3, wherein the plurality of quantities are displayed graphically.

5. The method of claim 3, wherein the plurality of quantities are displayed in a table.

6. The method of claim 1, wherein the performing the pivot shift test involves a plurality of iterations.

7. The method of claim 6, further comprising selecting a preferred iteration among the plurality of iterations.

8. A system that determines a medical condition involving bodily displacement, comprising:
   a memory configured to store computer-executable instructions; and
   a processor configured to execute the computer-executable instructions to perform operations, comprising:
     recording a plurality of images over a time period during a pivot shift test of a knee of a patient, wherein the images capture motion of three identifiable points of the knee during the pivot shift test, wherein the three identifiable points include a first point located at a Gerdy's tubercle of the patient, a second point located at a fibular head of the patient, and a third point located at a lateral epicondyle of a femur of the patient;
     determining a plurality of quantities based on the three identifiable points from consecutive frames from the plurality of images, wherein each of the quantities is a femoral anteroposterior position from Gerdy's point of the femur that is determined from a respective one of the consecutive frames and that is calculated by (i) determining a pivot point for the respective one of the consecutive frames, wherein the pivot point is a point where a first line from the first point intersects a second line between the second point and the third point, with the first line being perpendicular to the second line, (ii) determining a first linear distance from the third point to the pivot point for the respective one of the consecutive frames, (iii) determining a second linear distance from the second point to the third point for the respective one of the consecutive frames, (iv) determining a ratio of the first linear distance to the second linear distance for the respective one of the consecutive frames, and (v) determining the quantity for the respective one of the consecutive frames based on the ratio;

determining a medical condition diagnosis based a plurality of the quantities; and generating at least one of a tabulated or graphical quantification of abnormal movement based on the quantities, wherein the at least one of the tabulated or graphical quantification of abnormal movement facilitates grading the medical condition diagnosis based on comparing a magnitude based on one or more of the quantities to a predetermined condition.

9. The system of claim 8, wherein the operations further comprise:
optimizing the plurality of images.

10. The system of claim 9, wherein the plurality of images form at least a part of a video file.

11. The system of claim 10, wherein the operations further comprise:
obtaining from the video file a plurality of still images forming the consecutive frames.

12. The system of claim 8, wherein the operations further comprise:
identifying a plurality of markers associated with the three points related to the body part.

13. The system of claim 8, wherein the operations further comprise:
scaling the plurality of images based on known units.

14. The system of claim 13, wherein the operations further comprise:
establishing the scale based on at least one provided dimension within the plurality of images.

15. The system of claim 14, wherein the at least one provided dimension is a size of a marker.

16. A system, comprising:
means for recording a video during a pivot shift test of a knee of a patient, wherein the video capture motion of three identifiable points of the knee during the pivot shift test, wherein the three identifiable points include a first point located at a Gerdy's tubercle of the patient, a second point located at a fibular head of the patient, and a third point located at a lateral epicondyle of a femur of the patient;

means for determining a plurality of quantities based on the three identifiable points from consecutive frames from the video, wherein each of the quantities is a femoral anteroposterior position from Gerdy's point of the femur that is determined from a respective one of the consecutive frames and that is calculated by (i) determining a pivot point for the respective one of the consecutive frames, wherein the pivot point is a point where a first line from the first point intersects a second line between the second point and the third point, with the first line being perpendicular to the second line, (ii) determining a first linear distance from the third point to the pivot point for the respective one of the consecutive frames, (iii) determining a second linear distance from the second point to the third point for the respective one of the consecutive frames, (iv) determining a ratio of the first linear distance to the second linear distance for the respective one of the consecutive frames, and (v) determining the quantity for the respective one of the consecutive frames based on the ratio; and means for generating at least one of a tabulated or graphical quantification of abnormal movement based on the quantities, wherein the at least one of the tabulated or graphical quantification of abnormal movement facilitates determining a grade of a medical condition based on one or more of the quantities and a predetermined condition.

17. The system of claim 8, wherein the grading the medical condition diagnosis is based on the quantities as a function of time.

18. The method according to claim 1, wherein the first point is marked by a first marker positioned at the Gerdy's tubercle, the second point is marked by a second marker positioned at the fibular head, and the third point is marked by a third marker positioned at the lateral epicondyle, wherein in determining the plurality of quantities the first point is identified by a centroid of the first marker calculated from marker outline data obtained from the first marker, the second point is identified by a centroid of the second marker calculated from marker outline data obtained from the second marker, and the third point is identified by a centroid of the third marker calculated from marker outline data obtained from the third marker.

19. The system according to claim 8, wherein the first point is marked by a first marker positioned at the Gerdy's tubercle, the second point is marked by a second marker positioned at the fibular head, and the third point is marked by a third marker positioned at the lateral epicondyle, wherein in determining the plurality of quantities the first point is identified by a centroid of the first marker calculated from marker outline data obtained from the first marker, the second point is identified by a centroid of the second marker calculated from marker outline data obtained from the second marker, and the third point is identified by a centroid of the third marker calculated from marker outline data obtained from the third marker.

20. The system according to claim 16, wherein the first point is marked by a first marker positioned at the Gerdy's tubercle, the second point is marked by a second marker positioned at the fibular head, and the third point is marked by a third marker positioned at the lateral epicondyle, wherein in determining the plurality of quantities the first point is identified by a centroid of the first marker calculated from marker outline data obtained from the first marker, the second point is identified by a centroid of the second marker calculated from marker outline data obtained from the second marker, and the third point is identified by a centroid of the third marker calculated from marker outline data obtained from the third marker.

* * * * *